(12) United States Patent
Zhang et al.

(10) Patent No.: US 9,285,342 B2
(45) Date of Patent: Mar. 15, 2016

(54) ION MOBILITY SPECTROMETER SYSTEM (71) Applicant: Nuctech Company Limited, Beijing (CN)

(72) Inventors: Qingjun Zhang, Beijing (CN); Shiping Cao, Beijing (CN); Yuanjing Li, Beijing (CN); Zhiqiang Chen, Beijing (CN); Ziran Zhao, Beijing (CN); Yinong Liu, Beijing (CN); Jianping Chang, Beijing (CN); Yan Zheng, Beijing (CN); Yanchun Wang, Beijing (CN); Shaoji Mao, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 14/525,058

(22) Filed: Oct. 27, 2014

(65) Prior Publication Data
US 2015/0115152 A1 Apr. 30, 2015

(30) Foreign Application Priority Data

Oct. 28, 2013 (CN) .......................... 2013 1 0516808

(51) Int. Cl.
*G01N 30/72* (2006.01)
*H01J 49/04* (2006.01)
*G01N 27/62* (2006.01)

(52) U.S. Cl.
CPC .......... *G01N 27/622* (2013.01); *G01N 30/7206* (2013.01); *H01J 49/0422* (2013.01); *H01J 49/0468* (2013.01)

(58) Field of Classification Search
CPC ... G01N 27/622; G01N 30/7206; G01N 1/02; G01N 30/72; H01J 49/0422; H01J 49/004; H01J 49/0095; H01J 49/0468; H01J 49/14; H01J 49/40
See application file for complete search history.

(56) References Cited

U.S. PATENT DOCUMENTS

| 4,266,127 | A | * | 5/1981 | Chang | H01J 49/145 250/281 |
| 4,445,038 | A | * | 4/1984 | Spangler | G01N 27/622 250/287 |
| 5,227,628 | A | * | 7/1993 | Turner | G01N 27/622 250/282 |
| 5,543,331 | A | * | 8/1996 | Puumalainen | G01N 27/66 250/382 |
| 5,811,059 | A | | 9/1998 | Genovese et al. | |
| 6,239,428 | B1 | * | 5/2001 | Kunz | 250/287 |

(Continued)

FOREIGN PATENT DOCUMENTS

| CN | 201141853 Y | | 10/2008 | |
| CN | 201917559 U | * | 8/2011 | ............. G01N 30/02 |
| CN | 101728208 B | | 9/2012 | |

*Primary Examiner* — Michael Logie
(74) *Attorney, Agent, or Firm* — Knobbe, Martens, Olson & Bear, LLP (57) ABSTRACT

An ion mobility spectrometer system is disclosed. In one aspect, the system includes a gas chromatograph, first and second ion mobility spectrometers, and a sample feed device that feeds a sample from the gas chromatograph to the first and second ion mobility spectrometers. The sample feed device includes an inner chamber, first and second sample outlets for outputting the sample from the gas chromatograph to the first and second ion mobility spectrometers, respectively, and a gas inlet for inputting a gas into the sample feed device. The system detects and identifies molecules at improved resolution and enhanced molecule information. The system detects positive and negative ions, interrelates positive-mode and negative-mode spectrums, and separates substances.

14 Claims, 4 Drawing Sheets

(56) References Cited

U.S. PATENT DOCUMENTS

| | | | |
|---|---|---|---|
| 6,653,627 B2 * | 11/2003 | Guevremont et al. | 250/288 |
| 6,815,671 B2 * | 11/2004 | Johnston et al. | 250/287 |
| 7,259,369 B2 * | 8/2007 | Scott | G01N 27/622 250/281 |
| 7,361,206 B1 * | 4/2008 | Jahn | B01D 53/268 73/23.37 |
| 7,608,818 B2 | 10/2009 | Miller et al. | |
| 8,013,297 B2 * | 9/2011 | Peng et al. | 250/296 |
| 8,288,718 B2 * | 10/2012 | Li et al. | 250/288 |
| 8,362,419 B2 * | 1/2013 | Mitko | 250/286 |
| 8,921,772 B2 * | 12/2014 | Verenchikov | 250/281 |
| 2005/0056776 A1 * | 3/2005 | Willoughby | H01J 49/164 250/288 |
| 2006/0192103 A1 * | 8/2006 | Landgraf | 250/287 |
| 2007/0176092 A1 * | 8/2007 | Miller et al. | 250/288 |
| 2009/0114812 A1 * | 5/2009 | Landgraf | 250/282 |
| 2009/0283694 A1 * | 11/2009 | Chen et al. | 250/423 R |
| 2010/0314548 A1 * | 12/2010 | Munchmeyer et al. | 250/375 |
| 2011/0133072 A1 * | 6/2011 | Li et al. | 250/282 |
| 2012/0143515 A1 * | 6/2012 | Norman et al. | 702/24 |
| 2013/0161509 A1 * | 6/2013 | Munchmeyer et al. | 250/282 |
| 2015/0185190 A1 * | 7/2015 | Zhang et al. | 250/288 |

\* cited by examiner

ION MOBILITY SPECTROMETER SYSTEM

CROSS-REFERENCE TO RELATED APPLICATIONS

This application claims priority to Chinese Patent Application No. 201310516808.0, filed on Oct. 28, 2013, entitled "ION MOBILITY SPECTROMETER SYSTEM," which is incorporated herein by reference in its entirety.

BACKGROUND

1. Technological Field

The disclosed technology relates to an ion mobility spectrometer system, and more particularly to an ion mobility spectrometer system comprising a gas chromatograph and two ion mobility spectrometers.

2. Description of the Related Technology

U.S. Pat. No. 7,608,818 B2 discloses a system using a chromatograph in combination with a field asymmetric ion mobility spectrometer. This system is advantageous in that the ion mobility spectrometer has a small volume and a high detection sensitivity, and can separate ions by an electric field. However, this system has a worse separation capacity than a conventional ion mobility spectrometer and cannot effectively separate a multicomponent composition. U.S. Pat. No. 5,811,059 discloses a gas analyzing apparatus which comprises a gas chromatograph and a single-mode ion mobility spectrometer. This apparatus has a better separation capacity than the system disclosed in U.S. Pat. No. 7,608,818 B2, but can only detect charged particles of a single polarity and cannot detect substances having opposite electroaffinities.

SUMMARY OF CERTAIN INVENTIVE ASPECTS

The disclosed technology relates to an ion mobility spectrometer system comprising a gas chromatograph and two ion mobility spectrometers. For example, the ion mobility spectrometer system can effectively improve a resolving power, and enhance molecule information relevance, thereby identifying molecules to be detected more accurately.

One aspect of the disclosed technology is an ion mobility spectrometer system. The system includes a gas chromatograph configured to separate compounds and output a sample. The system includes a first ion mobility spectrometer and a second ion mobility spectrometer, each configured to identify ionized molecules. The system includes a sample feed device configured to input the sample. The sample feed device includes an inner chamber. The sample feed device includes a first sample outlet and a second sample outlet for outputting the inputted sample to the first ion mobility spectrometer and the second ion mobility spectrometer, respectively. The sample feed device includes a gas inlet for inputting a gas into the sample feed device.

For an embodiment of the disclosed technology, the ion mobility spectrometer system further includes a gas source connected to the gas chromatograph to supply a carrier gas to the gas chromatograph.

For an embodiment of the disclosed technology, the ion mobility spectrometer system further includes a pump inputting gas through the gas inlet of the sample feed device into the sample feed device, a first portion of the gas flowing from the sample feed device through the first sample outlet into the first ion mobility spectrometer, and a second portion of the gas flowing from the sample feed device through the second sample outlet into the second ion mobility spectrometer. For some embodiments, the first portion of the gas flows through a first gas inlet into the first ion mobility spectrometer and through a first gas outlet out of the first ion mobility spectrometer. For some embodiments, the second portion of gas flows through a second gas inlet into the second ion mobility spectrometer and through a second gas outlet out of the second ion mobility spectrometer.

For an embodiment of the disclosed technology, the inner chamber includes a first passage connected to an output pipe of the gas chromatograph. The inner chamber includes a second passage in fluid communication with the gas inlet of the sample feed device. The inner chamber includes a third passage in fluid communication with the first sample outlet. The inner chamber includes a fourth passage in fluid communication with the second sample outlet.

For an embodiment of the disclosed technology, the first and second passages are disposed substantially in a first straight line, and the third and fourth passages are disposed substantially in a second straight line.

For an embodiment of the disclosed technology, the first and second straight lines substantially intersect.

For an embodiment of the disclosed technology, the output pipe of the gas chromatograph is inserted in the inner chamber of the sample feed device.

For an embodiment of the disclosed technology, the sample feed device further includes a glass bushing disposed in the inner chamber.

For an embodiment of the disclosed technology, the sample feed device further includes a liner tube disposed in the inner chamber, the first and second sample outlets are disposed at both ends of the liner tube, respectively. For an embodiment of the disclosed technology, a branch pipe is disposed at a middle portion of the liner tube, the gas inlet of the sample feed device is disposed at an end of the branch pipe, and the output pipe of the gas chromatograph is in fluid communication with the liner tube.

For an embodiment of the disclosed technology, the output pipe of the gas chromatograph is inserted in the branch pipe.

For an embodiment of the disclosed technology, the liner tube and the branch pipe are made of glass.

For an embodiment of the disclosed technology, the output pipe of the gas chromatograph is inserted in the branch pipe through the gas inlet of the sample feed device.

For an embodiment of the disclosed technology, the output pipe of the gas chromatograph is inserted in the branch pipe through an opening of the liner tube on an opposite side to the gas inlet of the sample feed device.

Another aspect of the disclosed technology is an ion mobility spectrometer system. The system includes means for separating compounds and outputting a sample. The system includes means for identifying ionized molecules. The system includes means for inputting the sample, comprising means for outputting the inputted sample to the identifying means, and means for inputting a gas into the sample inputting means.

For an embodiment of the disclosed technology, the separating means includes a gas chromatograph. The identifying means includes a first ion mobility spectrometer and a second ion mobility spectrometer. The sample inputting means includes a sample feed device. The outputting inputted sample means includes a first sample outlet and a second sample outlet. The gas inputting means includes a gas inlet.

Embodiments of the disclosed technology may effectively improve a resolving power and enhance molecule information relevance, thereby identifying molecules to be detected more accurately. In addition, an ability of the ion mobility spectrometer system to detect positive and negative ions interrelates positive-mode and negative-mode spectrums, and the ion mobility spectrometer system has a higher ability to separate some substances than a single-mode ion mobility spectrometer which achieves positive and negative modes by switching a drift voltage.

BRIEF DESCRIPTION OF THE DRAWINGS

The following figures illustrate implementations of the disclosed technology. The figures and implementations provide some embodiments of the disclosed technology in a non-limiting and non-exclusive manner.

DETAILED DESCRIPTION OF CERTAIN ILLUSTRATIVE EMBODIMENTS

The following detailed description is directed to certain specific embodiments of the disclosed technology. However, the disclosed technology can be embodied in a multitude of different ways. It should be apparent that the aspects herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein.

The described embodiments are just intended for illustrating rather than limiting the disclosed technology. Numerous specific details are illustrated for a clear and thorough understanding of the disclosed technology. It is apparent to those skilled in the art that these specific details are not necessary for implementation of the disclosed technology. Detailed description of known structures, circuits, materials or methods are omitted which otherwise may obscure the disclosed technology.

Throughout the specification, reference to "an embodiment," "embodiments," "an example" or "examples" means that particular features, structures or characteristics described in connection with such embodiment or example are contained in at least one embodiment of the disclosed technology. The phrase "an embodiment," "embodiments," "an example" or "examples" in various places throughout the specification does not necessarily refer to the same embodiment or example. Further, the particular features, structures or characteristics may be contained in one or more embodiments or examples in any appropriate combination and/or sub-combination. Those skilled in the art will appreciate that the term "and/or" herein indicates any or all combinations of one or more of the listed items.

Figure 1:
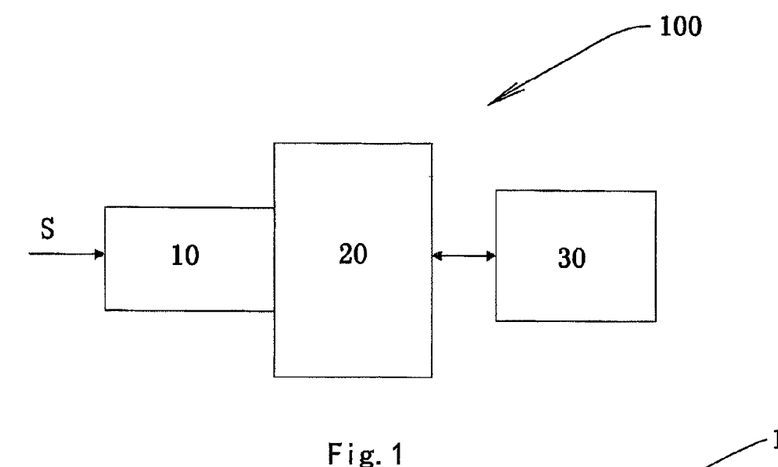
FIG. 1 is a schematic diagram of an ion mobility spectrometer system according to an embodiment of the disclosed technology.
Figure 2:
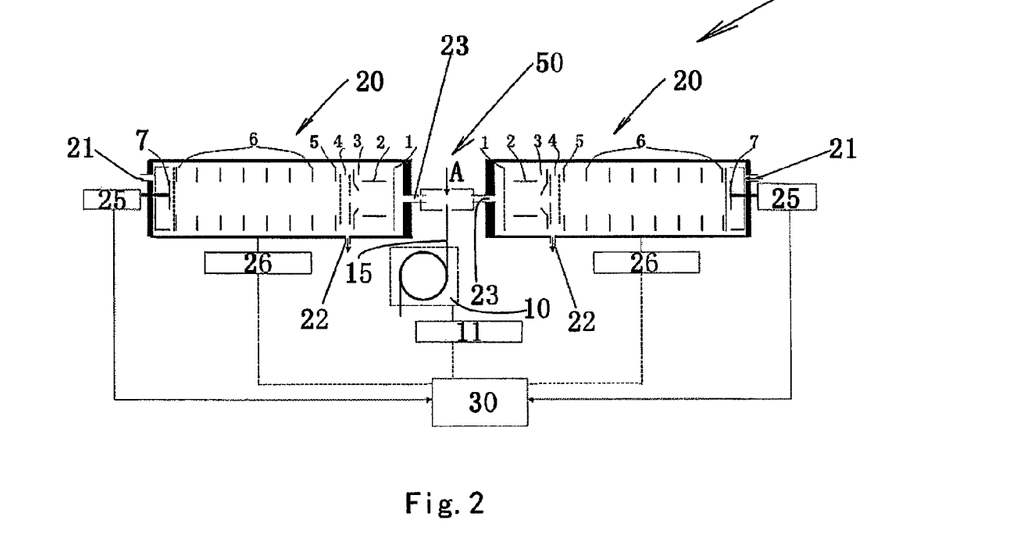
FIG. 2 is a schematic diagram showing a connection of an ion mobility spectrometer system according to an embodiment of the disclosed technology.
Figure 3:
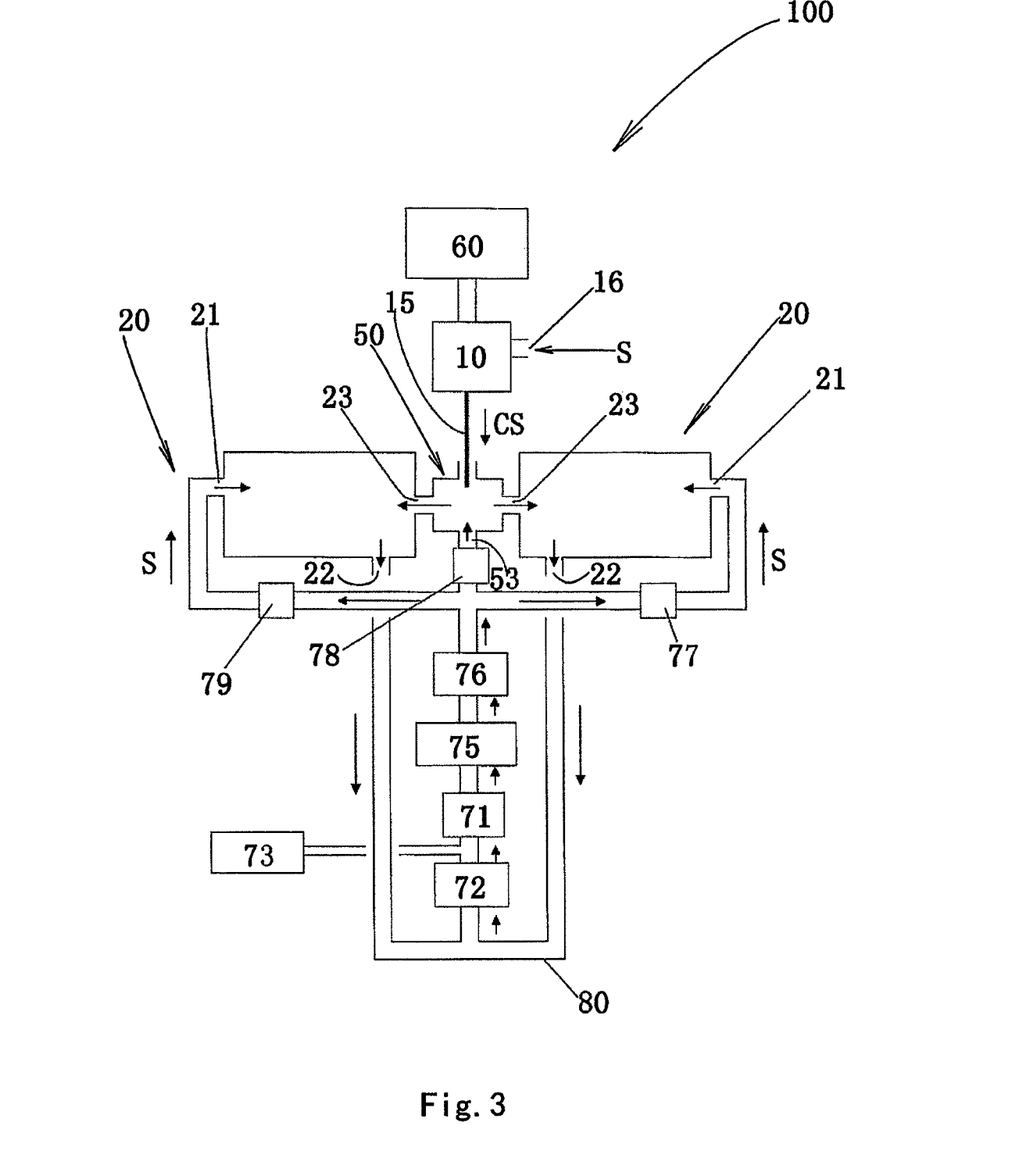
FIG. 3 is a schematic diagram showing a gas path of an ion mobility spectrometer system according to an embodiment of the disclosed technology.

As shown in FIGS. 1-3, an ion mobility spectrometer system 100 according to an embodiment of the disclosed technology comprises a gas chromatograph (GC) 10, a dual-mode ion mobility spectrometer (IMS) 20 or a first ion mobility spectrometer 20 and a second ion mobility spectrometer 20 (such as first and second coaxial ion mobility spectrometers 20), a controller or control system 30, and a sample feed device 50. The sample feed device 50 is configured to input a sample S (such as a gas CS including a sample S and a carrier gas, or a high-pressure gas CS including a sample S and a carrier gas) outputted from the gas chromatograph 10 into the first ion mobility spectrometer 20 and the second ion mobility spectrometer 20. As shown in FIG. 3, the ion mobility spectrometer system 100 further comprises a gas source 60 connected to the gas chromatograph 10, for example through a pipe, to supply a gas such as a carrier gas to the gas chromatograph 10. After the gas CS including the sample S and the carrier gas is outputted from the gas chromatograph 10, it enters the sample feed device 50 through an output pipe 15 of the gas chromatograph 10.

The gas chromatograph 10 may be any gas chromatograph that, for example, separates and analyzes compounds that may be vaporized without decomposition. As shown in FIGS. 1-3, the gas chromatograph 10 comprises a sample inlet 16 for inputting the sample S, and the ion mobility spectrometer system 100 further comprises a drive circuit 11 for driving a heating and cooling device of the gas chromatograph 10.

The first ion mobility spectrometer 20 and the second ion mobility spectrometer 20 may be any ion mobility spectrometers that, for example, separates and identifies ionized molecules in the gas phase. For example, designs of the first and second ion mobility spectrometers 20 may be based on some of designs of the ion mobility spectrometer disclosed in CN101728208B, or the first and second ion mobility spectrometers may be the ion mobility spectrometer disclosed in CN201141853Y. Referring to FIG. 2, each ion mobility spectrometer 20 may comprise a mesh electrode 1, an ion source 2, a focusing guide electrode 3, a storage part 4, a first ring or mesh electrode 5, drift electrodes 6, and a Faraday plate 7 which are arranged in sequence and sealed in a tube. As shown in FIG. 2, the ion mobility spectrometer system 100 further comprises a high-voltage and ion gate circuit 26 for applying voltages to the mesh electrode 1, the ion source 2, the focusing guide electrode 3, the storage part 4, the first ring or mesh electrode 5, and the drift electrodes 6. Each ion mobility spectrometer system 100 further comprises a preamplifier circuit 25 for amplifying a signal outputted from the Faraday plate 7. In addition, each ion mobility spectrometer 20 further comprises a gas inlet 21 (such as a drift gas inlet), a gas outlet 22 (such as a drift gas outlet), and a sample inlet 23. A gas (such as a drift gas) enters the ion mobility spectrometer 20 through the gas inlet 21, the gas (such as the drift gas) flows out of the ion mobility spectrometer 20 through the gas outlet 22, and the carrier gas and the sample enter the ion mobility spectrometer 20 through the sample inlet 23.

As shown in FIG. 2, the entire GC-IMS system is an airtight system, and the gas flow circulated in the system is isolated from an outside of the system (since both macromolecules and moisture will adversely affect the system), which ensures that the system will not be subjected to interference from its environment during measuring and thus ensures measuring accuracy.

As shown in FIGS. 1-3, the controller or control system 30 is configured to perform control of heating and temperature programming of the GC. Control system 30 is configured to control a high voltage power supply, a power supply of the preamplifier circuit 25, heating, valves and a pump of the IMSs. Control system 30 is configured to transmit signals measured by the IMSs to a computer for analysis. The GC comprises a column oven, a sample injector, and a chromatographic column. The dual-mode IMS (for example, which may be constructed by two coaxial single-mode IMS drift tubes 20) comprises the high-voltage and ion gate circuit 26, the preamplifier circuit 25, a heating and temperature maintaining device (not shown), a pump 71, a molecular sieve 75, and buffers 72 and 76.

As shown in FIGS. 1-4, the sample feed device 50 comprises an inner chamber 51, a first sample outlet 52 and a second sample outlet 52 for outputting the sample S (or the gas CS including the sample S and the carrier gas) inputted from the gas chromatograph 10 into the first ion mobility spectrometer 20 and the second ion mobility spectrometer 20, respectively, and a gas inlet 53 for inputting the gas into the sample feed device 50. Specifically, the sample S, together with the gas, such as high-purity nitrogen gas, from the gas source 60 is outputted from the gas chromatograph 10 and enters the sample feed device 50.

Figure 4:
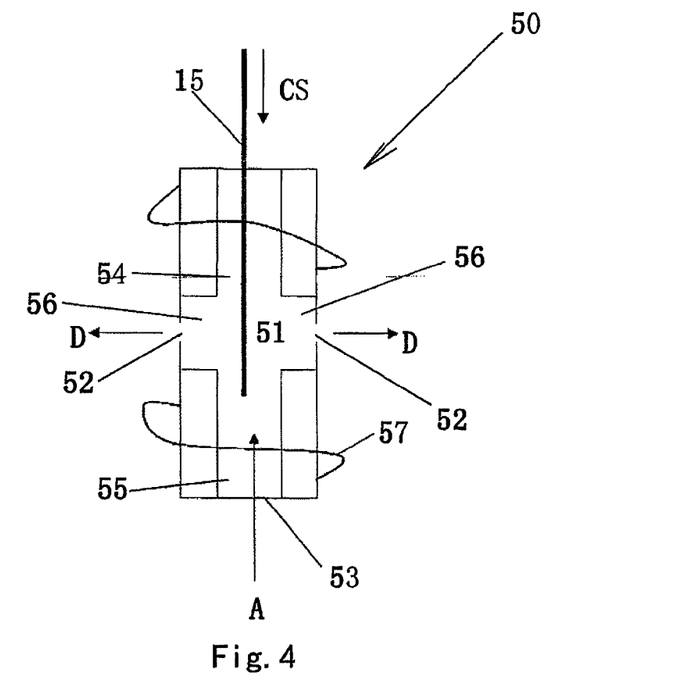
FIG. 4 is a schematic diagram showing a structure of a sample feed device of an ion mobility spectrometer system according to an embodiment of the disclosed technology.

As shown in FIGS. 2-4, the ion mobility spectrometer system 100 further comprises the buffer 72, the pump 71, the molecular sieve 75, the buffer 76, valves 77, 78, 79, and a relief valve 73. By the pump 71, the gas is inputted into the sample feed device 50 through the gas inlet 53 of the sample feed device 50, and flows from the sample feed device 50 into the first ion mobility spectrometer 20 and the second ion mobility spectrometer 20 through the first sample outlet 52 and the second sample outlet 52 respectively. The gas inputted into the sample feed device 50 through the gas inlet 53 of the sample feed device 50 may be referred to as a sweeping gas A. The sweeping gas A is used to cause the sample S (or the gas CS including the sample S and the carrier gas), inputted from the gas chromatograph 10, to flow into the first ion mobility spectrometer 20 and the second ion mobility spectrometer 20 through the first sample outlet 23 and the second sample outlet 23. In other words, the sweeping gas A blows or sweeps the sample S (or the gas CS), inputted from the gas chromatograph 10, into the first ion mobility spectrometer 20 and the second ion mobility spectrometer 20. In addition, pressures in the first ion mobility spectrometer 20 and the second ion mobility spectrometer 20 are lower than a pressure in the inner chamber 51 of the sample feed device 50. Therefore, the sample S (or the high-pressure gas CS including the sample S and the carrier gas) inputted from the gas chromatograph 10, and the gas (the sweeping gas A) inputted from the gas inlet 53 of the sample feed device 50 are mixed, and sucked, as a sucked gas flow D, into the first ion mobility spectrometer 20 and the second ion mobility spectrometer 20 through the first sample outlet 52 and the second sample outlet 52 and the sample inlets 23.

As shown in FIG. 3, the pump 71 has an output (a high-pressure side) connected to the molecular sieve 75 through a pipe 80, the molecular sieve 75 has an output connected to the buffer 76 through the pipe 80, and the buffer 76 is connected to the gas inlet 21 of the second ion mobility spectrometer 20, the gas inlet 53 of the sample feed device 50, and the gas inlet 21 of the first ion mobility spectrometer 20 via the valves 77, 78 and 79 through the pipe 80 respectively. The pump 71 has an input (a low-pressure side) connected to the buffer 72 and the relief valve 73 through the pipe 80, and the buffer 72 has an input connected to the gas outlets 22 of the first and second ion mobility spectrometers 20 through the pipe 80 respectively. In this way, the gas flows into the first ion mobility spectrometer 20 and the second ion mobility spectrometer 20 through the gas inlets 21 of the first ion mobility spectrometer 20 and the second ion mobility spectrometer 20 respectively, and flows out of the first ion mobility spectrometer 20 and the second ion mobility spectrometer 20 through the gas outlets 22 of the first ion mobility spectrometer 20 and the second ion mobility spectrometer 20 respectively.

As shown in FIG. 4, in inner chamber 51 of the sample feed device 50 may comprise a first passage 54 connected to an output pipe 15 of the gas chromatograph 10. Inner chamber 51 may comprise a second passage 55 in fluid communication with the gas inlet 53 of the sample feed device 50 (and is used for inputting the sweeping gas flow A). Inner chamber 51 may comprise third and fourth passages 56 in fluid communication with the first and second sample outlets 52, respectively. The first and second passages 54 and 55 are disposed substantially in a first straight line, and the third and fourth passages 56 are disposed substantially in a second straight line. The first and second straight lines substantially intersect. For example, the first and second straight lines are substantially perpendicular or oblique to each other. The output pipe 15 of the gas chromatograph 10 is inserted in the inner chamber 51 of the sample feed device 50.

As shown in FIG. 4, the first and second sample outlets 52 may be two holes having the same diameter, and disposed on both sides of the sample feed device. The diameter of the holes is within the range of 2 mm-1 cm. A smaller diameter of the holes can ensure that a positive pressure is formed within the sample feed device 50 with respect to drift regions of the ion mobility spectrometers. Ionization regions of the ion mobility spectrometers are located outside the sample feed device 50. A distance between the gas outlet 22 (a port for extracting the drift gas) and the ionization region of each ion mobility spectrometer 20 is only within the range of 1-2 cm. All of the gas flow in the drift tube of each ion mobility spectrometer flows from the gas outlet 22. The sample in the sample feed device 50 quickly enters the ionization regions of the drift tubes or the ion mobility spectrometers with the help of the extracted gas so as to be ionized. The sample feed device 50 needs to be heated by an additional heater 57 such as an electric heating wire to ensure a temperature within the sample feed device 50 is not less than a temperature of the chromatographic column of the gas chromatograph 10. Only in this way the gas flowing out of the gas chromatograph 10 will not condense in the sample feed device 50. An inner wall of the sample feed device 50 is smooth and is subjected to a deactivation process. In this way, reaction between active sample molecules and a material of the inner wall can be decreased or prevented, thereby ensuring that the sample molecules enter the ion mobility spectrometers without loss.

Figure 5:
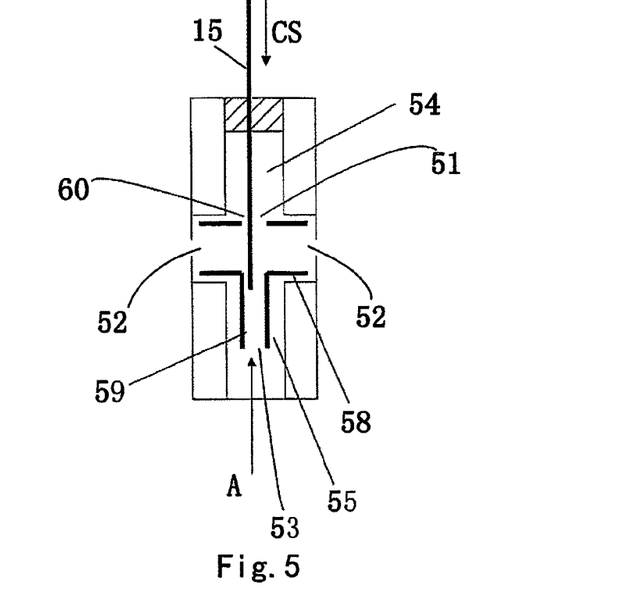
FIG. 5 is a schematic diagram showing an example of a sample feed device of an ion mobility spectrometer system according to an embodiment of the disclosed technology.
Figure 6:
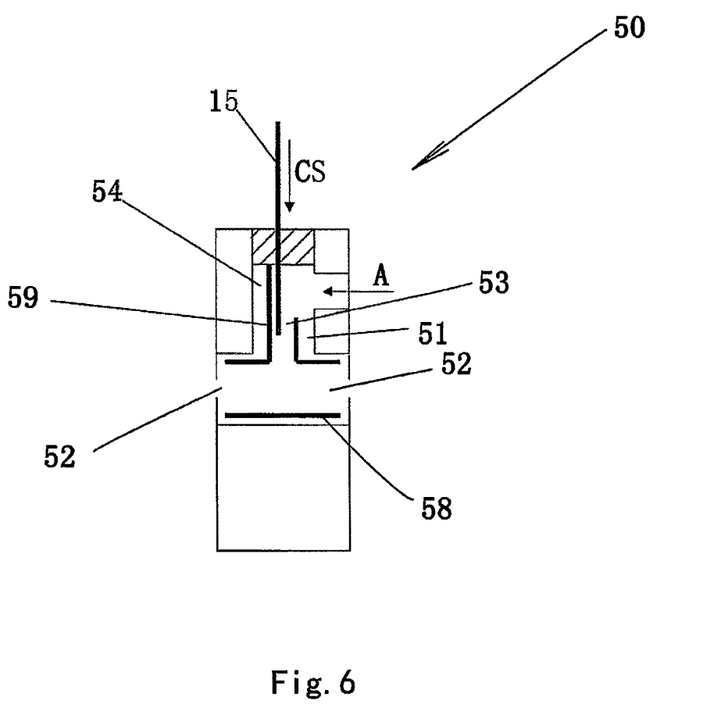
FIG. 6 is a schematic diagram showing another example of a sample feed device of a ion mobility spectrometer system according to an embodiment of the disclosed technology.

As shown in FIGS. 5-6, the sample feed device 50 further comprises a bushing, such as a glass bushing, disposed in the inner chamber 51. Alternatively, the sample feed device 50 may further comprise a liner tube 58 disposed in the inner chamber 51. A branch pipe 59 is disposed at a middle portion of the liner tube 58. The liner tube 58 and the branch pipe 59 may be made of glass. The first and second sample outlets 52 are disposed at both ends of the liner tube 58, respectively. The gas inlet 53 of the sample feed device 50 is disposed at an end of the branch pipe 59, and the output pipe 15 of the gas chromatograph 10 is in fluid communication with the liner tube 58. As shown in FIGS. 5-6, the output pipe 15 of the gas chromatograph 10 is inserted in the branch pipe 59. The output pipe 15 of the gas chromatograph 10 may be inserted in the branch pipe 59 through the gas inlet 53 of the sample feed device 50 or the output pipe 15 of the gas chromatograph 10 may be inserted in the branch pipe 59 through an opening 60 of the liner tube 58 on an opposite side to the gas inlet 53 of the sample feed device 50. Apparently, the output pipe 15 may be inserted in any appropriate position within the liner tube 58 or the inner chamber 51.

In the embodiment shown in FIG. 5, two ends of the liner tube 58 are in fluid communication with the positive-mode and negative-mode drift tubes or the first and second ion mobility spectrometers 20 respectively. The output pipe 15 of the chromatographic column of the gas chromatograph 10 is in fluid communication with the liner tube 58 through the opening 60. The sweeping gas flow A enters the liner tube 58 through an opening at the middle portion of the liner tube or the branch pipe 59. The inner wall of the liner tube 58 is smooth and will not react with any active molecules. Glass is a common material for chemical preparation. Design requirements can be easily satisfied and complicated processes such as polishing and deactivation of metal can be reduced or removed by adopting a glass tube as an inner wall of a gas mixing device.

In the embodiment shown in FIG. 6, the liner tube 58 may have an opening at its middle portion or the branch pipe 59. Two ends of the liner tube 58 are in fluid communication with the positive-mode and negative-mode drift tubes or the first and second ion mobility spectrometers 20 respectively. The output pipe 15 of the chromatographic column of the gas chromatograph 10 is in fluid communication with the liner tube 58 through the opening or the branch pipe 59. In addition, the sweeping gas A enters the sample feed device 50 through the same opening or branch pipe 59. The sweeping gas and the sample are mixed in the inner chamber 51 of the sample feed device. The passage 54 connected to the output pipe 15 of the chromatographic column of the gas chromatograph 10 and the passage for the sweeping gas flow A may be connected at any angle in the sample feed device.

A sample residence time measured by the gas chromatograph 10 is on the order of a minute (the narrowest peak width may be on the order of a second). A drift time measured by the IMS is on the order of a millisecond (the drift time is generally in the range from several milliseconds to tens of milliseconds and a width of a peak is less than a millisecond). Therefore, the gas chromatograph 10 can be used as a primary separation leading device of the IMS system. An output of the chromatographic column of the gas chromatograph 10 is connected directly to the sample feed device 50 for the dual-mode IMS or the two IMSs. The sample S and the carrier gas are mixed again in the sample feed device under the action of the gas flow in the sample feed device 50, and the mixed sample S and carrier gas flow into the two IMSs. After the sample enters the ionization regions of the two IMSs and is charged, it is stored in ion storage regions. The ions are released into the drift regions by opening ion gates or changing voltages of electrodes. Drift time information of the ions to be detected is acquired by measuring current signals outputted from the Faraday plates 7 and generated by the ions reaching the Faraday plates 7. Conventional radiation sources such as Ni63 may be adopted as the ionization sources of the ionization regions of the two positive-mode and negative-mode IMSs. The ionization sources such as corona discharge devices, glow discharge devices, laser ionization devices, and surface ionization devices may also be adopted. In some embodiments, the gas flow can be distributed from the gas chromatograph to the dual-mode IMS or the two IMSs such that the sample S flowing out of the gas chromatograph can be effectively transfected to the IMSs and can be distributed equally to the positive-mode and negative-mode drift tubes or the two IMSs. In the present embodiment, the gas flows are designed to be guided and include a stream of the sweeping gas A, the gas CS (i.e., the carrier gas and the sample S) from the GC, and two streams of the gas D extracted from the first and second IMSs. The sweeping gas A and the high-pressure gas CS containing the sample and flowing out of the GC are sufficiently mixed in the narrow inner chamber of the sample feed device 50. A positive-pressure region is formed in the inner chamber of the sample feed device and negative-pressure regions (relative to the inner chamber) are formed in the IMSs on both sides of the sample feed device 50, under the action of both the gas flows extracted from the first and second IMSs. Under the action of both the gas flows extracted from the first and second IMSs on both sides of the sample feed device, the sample S will enter the ionization regions of the IMSs on both sides of the sample feed device in a short time. In order that the sample is not adsorbed in the sample feed device, a temperature of the sample feed device is not less than a temperature of the GC. In the present embodiment, a gas path of the system is designed such that the relief valve 73 is disposed on an output side of the pump 71 to maintain an internal pressure of the system substantially constant. The whole gas path is an internal circulation system. A gas pressure and a flow rate are adjusted by the valves 77, 78, and 79 to maintain pressures and flow rates in the positive-mode and negative-mode drift tubes or the two IMSs substantially equal to each other and maintain the positive-mode and negative-mode drift tubes or the two IMSs in a negative-pressure state relative to the sample feed device.

The gas chromatograph-dual-mode ion mobility spectrometer system according to the embodiments of the disclosed technology can effectively improve separation ability and achieve simultaneous identification of positive and negative ions. In other words, the system can respond to almost all of macromolecules having electroaffinity, thereby improving a range of application of the system. In addition, in the connection part (i.e., the sample feed device) between the GC and IMSs, the gas flows are designed to be guided. In this way, the sample and background gas for IMSs are sufficiently mixed and then equally distributed to the positive-mode and negative mode IMSs. In the inner chamber of the sample feed device as a gas flow mixing region, an inner wall of the sample feed device is subjected to a deactivation process (or an inert material is adopted for the inner wall) to reduce a probability of possible reaction between the sample molecules and the inner wall. Furthermore, the inner wall is smooth and has no burr to reduce adsorption and detention of the sample in the connection part, thereby achieving effective transfer of the sample from the GC to the IMSs.

In the embodiment, the two IMSs are connected by a narrow inner chamber of the sample feed device. A high-speed positive-pressure gas CS flowing out of the GC and the sweeping gas flow A of a flow rate of 0.5 L/min or less are mixed in the inner chamber 51 of the sample feed device 50 so that the inner chamber 51 is in a positive pressure state. The mixed sample and gas enter the ionization regions of the positive-mode and negative-mode IMSs through the first sample outlet 52 and the second sample outlet 52, such as small holes, on both sides of the sample feed device. Since the IMSs are in a negative-pressure state, and the port for extracting the drift gas is close to the ion gate or electrodes in each IMS, the sample molecules will flow into the ionization region in an axial direction of the IMS in each IMS quickly. In each IMS, the ionized sample molecules are stored in a conical storage region, and enter the drift region when the ion gate is opened or voltages of the electrodes are changed, and the charged ions reach the Faraday plate under the action of an electric field of the drift region (referring to CN101728208B and CN201141853Y). The drift times of the ions varies depending upon mobility, thereby achieving distinguishing and identification. A weak electrical signal generated in the Faraday plate 7 is amplified by an amplifier circuit 27 and analog-to-digital converted, and then transmitted to a computer for data processing. In one complete detection, the system simultaneously records the residence time (of which a unit is the minute or even the second) of the sample in the GC, and a spectrum of amplitude versus drift time (several milliseconds or tens of milliseconds) measured by each IMS. Each IMS continuously measures substance flowing out of the GC in each second, and finally a three-dimensional spectrum of residence time versus drift time versus amplitude is plotted on the computer. The three-dimensional spectrum can enhance the separation ability of the system. In other words, some substances that cannot be separated by the GC can be separated by the IMS, and vice versa. The dual-mode IMS-GC system can simultaneously measure positive and negative ions. For those substances that can simultaneously generate positive and negative ions (many suspicious macromolecules belong to this type of substance), the system will have four-dimensional separation ability to detect, identify, and resolve substances.

FIG. 3 is a diagram showing a connection of the gas path of the system 100. In FIG. 3, the arrows indicate directions of the flows. High-purity nitrogen gas (or gas commonly used for the GC such as hydrogen gas) is stably supplied to the chromatographic column or the gas chromatograph 10, and the high-pressure gas CS flows out of the gas chromatograph 10 and then enters the sample feed device 50. The pump 71 drives the gas flows of the entire system to move. The gas flowing from an outlet of the pump 71 are filtered through the molecular sieve 75 so that moisture and foreign gas molecules are filtered out and then enter the buffer 76 such as a buffer tank. The gas flowing out of the buffer 76 is divided into three streams of gas through a three-way pipe. Two of the three streams of gas enter the positive-mode and negative-mode drift tubes or the two IMSs 20 through the gas inlets 21 and 21 at ends thereof as drift gas flows, respectively, and the remaining one of the three streams of gas enters the sample feed device 50 through the gas inlet 53 as the sweeping gas flow A. The flow rates of the three streams of gas are controlled by the valves 77, 78, and 79. The gas CS and the sweeping gas flow A are mixed in the sample feed device 50 and then enter the positive-mode and negative-mode drift tubes or the two IMSs 20 through the first sample outlet 52 and the second sample outlet 52 (such as two small holes having the same diameter). The gas in the drift tubes or the first and second IMSs 20 is extracted back to the pump 71 through the gas outlets 22 close to the ion gate or the electrodes. In this way, a self-circulation is completed. In order to ensure that the internal gas pressure of the system can be substantially equal to a stable value or can be stable, the relief valve 73 is disposed at the outlet of the pump 71. When the internal pressure is higher than a predetermined value, the system automatically releases the pressure. However, in fact, the flow rate of the gas flowing out of the gas chromatograph 10 is very small relative to the flow rate of the IMSs, and the gas or the gas pressure will leak slowly from sealing portions of the system. Therefore, change of the internal gas pressure of the system by the flow rate of the gas flowing out of the GC 10 can be ignored. The valves are used in the gas path to control the flow rates at respective points and the internal gas pressure of the system such that the flow speed of the gas flow and the pressure in the positive-mode drift tube or one of the two IMSs are substantially equal to the flow speed of the gas flow and the pressure in the negative-mode drift tube or the other one of the two IMSs, respectively, while the pressure in the inner chamber of the sample feed device is maintained higher than the gas pressures in the positive-mode and negative-mode drift tubes or the two IMSs.

It should be understood that any reference to an element herein using a designation such as "first," "second," and so forth does not generally limit the quantity or order of those elements. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of: A, B, or C" used in the description or the claims means "A or B or C or any combination of these elements."

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the disclosed technology may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

It is to be understood that the claims are not limited to the precise configuration and components illustrated above. Various modifications, changes and variations may be made in the arrangement, operation and details of the methods and apparatus described above without departing from the scope of the claims.

What is claimed is:

1. An ion mobility spectrometer system, comprising:
   a gas chromatograph configured to separate compounds and output a sample;
   a first ion mobility spectrometer and a second ion mobility spectrometer, each configured to identify ionized molecules; and
   a sample feed device configured to input the sample, the sample feed device comprising:
     an inner chamber;
     a first sample outlet and a second sample outlet for outputting the inputted sample to the first ion mobility spectrometer and the second ion mobility spectrometer, respectively;
     a gas inlet for inputting a sweeping gas into the sample feed device; and
     a glass bushing disposed in the inner chamber.

2. The ion mobility spectrometer system of claim 1, further comprising a gas source connected to the gas chromatograph to supply a carrier gas to the gas chromatograph.

3. The ion mobility spectrometer system of claim 1, further comprising a pump inputting gas through the gas inlet of the sample feed device into the sample feed device, a first portion of the gas flowing from the sample feed device through the first sample outlet into the first ion mobility spectrometer, a second portion of the gas flowing from the sample feed device through the second sample outlet into the second ion mobility spectrometer.

4. The ion mobility spectrometer system of claim 3, wherein the first portion of the gas flows through a first gas inlet into the first ion mobility spectrometer and through a first gas outlet out of the first ion mobility spectrometer, wherein the second portion of gas flows through a second gas inlet into the second ion mobility spectrometer and through a second gas outlet out of the second ion mobility spectrometer.

5. The ion mobility spectrometer system of claim 1, wherein the inner chamber comprises:
   a first passage connected to an output pipe of the gas chromatograph;
   a second passage in fluid communication with the gas inlet of the sample feed device;
   a third passage in fluid communication with the first sample outlet; and
   a fourth passage in fluid communication with the second sample outlet.

6. The ion mobility spectrometer system of claim 5, wherein the first passage and the second passage are disposed substantially in a first straight line, and wherein the third passage and the fourth passage are disposed substantially in a second straight line.

7. The ion mobility spectrometer system of claim 6, wherein the first and second straight lines substantially intersect.

8. The ion mobility spectrometer system of claim 1, wherein the output pipe of the gas chromatograph is inserted in the inner chamber of the sample feed device.

9. The ion mobility spectrometer system of claim 1, the sample feed device further comprising a heater for heating the sample feed device.

10. An ion mobility spectrometer system, comprising:
    a gas chromatograph configured to separate compounds and output a sample;
    a first ion mobility spectrometer and a second ion mobility spectrometer, each configured to identify ionized molecules; and
    a sample feed device configured to input the sample, the sample feed device comprising:
      an inner chamber;
      a first sample outlet and a second sample outlet for outputting the inputted sample to the first ion mobility spectrometer and the second ion mobility spectrometer, respectively;
      a gas inlet for inputting a sweeping gas into the sample feed device;
      a liner tube disposed in the inner chamber, the first sample outlet and the second sample outlet disposed at both ends of the liner tube, respectively; and
      a branch pipe disposed at a middle portion of the liner tube, the gas inlet of the sample feed device disposed at an end of the branch pipe, an output pipe of the gas chromatograph in fluid communication with the liner tube.

11. The ion mobility spectrometer system of claim 10, wherein the output pipe of the gas chromatograph is inserted in the branch pipe.

12. The ion mobility spectrometer system of claim 10, wherein the liner tube and the branch pipe are made of glass.

13. The ion mobility spectrometer system of claim 10, wherein the output pipe of the gas chromatograph is inserted in the branch pipe through the gas inlet of the sample feed device.

14. The ion mobility spectrometer system of claim 10, wherein the output pipe of the gas chromatograph is inserted in the branch pipe through an opening of the liner tube on an opposite side to the gas inlet of the sample feed device.

* * * * *